United States Patent [19]

Becker et al.

[11] 4,416,812
[45] Nov. 22, 1983

[54] METHOD OF PREPARING TISSUE THROMBOPLASTIN

[75] Inventors: Udo Becker, Munich; Eugen Schaich, Weilheim; Manfred Weigert, Tutzing, all of Fed. Rep. of Germany

[73] Assignee: Boehringer Mannheim GmbH, Mannheim-Waldhof, Fed. Rep. of Germany

[21] Appl. No.: 446,088

[22] Filed: Dec. 1, 1982

[30] Foreign Application Priority Data

Dec. 21, 1981 [DE] Fed. Rep. of Germany ....... 3150596

[51] Int. Cl.³ .................. C07G 7/00; C07G 7/026
[52] U.S. Cl. ........................... 260/112 R; 260/112 B; 424/95; 424/101; 424/105; 435/13; 435/212
[58] Field of Search .................. 260/112 R, 112 B; 424/95, 101, 105; 435/13, 212

[56] References Cited

U.S. PATENT DOCUMENTS

| 2,842,480 | 7/1958 | Singher et al. | 260/112 B X |
|---|---|---|---|
| 2,847,348 | 8/1958 | Singher et al. | 435/212 |
| 2,847,350 | 8/1958 | Singher et al. | 435/212 X |
| 2,921,000 | 1/1960 | Singher et al. | 435/13 X |
| 3,228,841 | 1/1966 | Cohen et al. | 435/13 |
| 3,522,148 | 7/1970 | Adam et al. | 435/13 |
| 3,980,432 | 9/1976 | Trobisch et al. | 435/13 |
| 3,983,004 | 9/1976 | Trobisch et al. | 435/13 |

OTHER PUBLICATIONS

Thrombosis Hemostasis, 1939, 592–599, (1978), Stuttgart.
Biochem. Soc. Trans. 8, 133, (1980), Gardiner et al.
'Human Blood Coagulation, Hemostasis and Thrombosis', (R. Biggs Editor, Oxford), 1976, p. 663.

Primary Examiner—Howard E. Schain
Attorney, Agent, or Firm—Felfe & Lynch

[57] ABSTRACT

A tissue thromboplastin preparation which is sensitive to coagulation factor VII, is prepared from acetone dry powder mammalian tissue, by extraction with a salt solution containing 1 to 20 mmol/1 of calcium ions and, if desired, a surface active agent, after which the extract maybe dried.

10 Claims, No Drawings

METHOD OF PREPARING TISSUE THROMBOPLASTIN

BACKGROUND OF THE INVENTION

The invention relates to the preparation of a thromboplastin (TP) of specific factor VII sensitivity from mammalian tissue.

The term TP is to be understood, in accordance with DIN No. 58910, to mean an extract from mammalian tissue, which, in the presence of calcium ions, greatly shortens the coagulation time of blood plasma.

Thromboplastins are used diagnostically for the identification of coagulation abnormalities. The test used is referred to as Quick's test or the prothrombin time test. The events occurring in the case of a blood vessel injury, which ultimately lead to blood coagulation and to the closing of the vessel wound, are simulated by adding blood or blood plasma from the patient to tissue TP in the presence of calcium, and measuring the time it takes for a coagulum to form. The TP activates factor VII, which in turn brings about, through factors X and V, the formation of thrombin from prothrombin (factor II). Thrombin cleaves the fibrinogen to insoluble fibrin which participates in the closing of the wound. The time it takes after the addition of thromboplastin plus calcium for the formation of a clot is a measure of the concentration or activity of the coagulation factors involved.

Quick's test thus provides a summary knowledge of the concentration ratios of the coagulation enzymes (factors) involved. However, for the same Quick test values, the concentrations of the individual factors II, V, VII and X can be present in a great variety of ratios. Such alterations the concentration ratios of individual coagulation factors can be used, for example, by pathological changes (cirrhosis of the liver, intravascular clotting, vitamin deficiencies), or by medication, such as coumarin derivatives administered as oral anticoagulants. Differences become evident when the same test material is tested with thromboplastins from different manufacturers. These generally differ greatly in their sensitivity to individual coagulation factors, so that the same sample from a patient can have different prothrombin times when tested with TP from different manufacturers.

Therefore, it is desirable to achieve comparability between different thromboplastins. One way to accomplish this is standardization in reference to a particular factor sensitivity. There are numerous methods for the preparation of factor-sensitive TP. While the production of preparations sensitive to factors II, V and X presents no particular problem, difficulty still is encountered in the preparation of thromboplastin sensitive to factor VII.

It is assumed that a low factor-sensitivity of a thromboplastin is due to the fact that the preparation still contains traces of coagulation factors which are brought in through the blood content of the tissue used for the extraction of the thromboplastin. This assumption is supported especially by a finding reported in Thrombosis Hemostasis (Stuttgart) 1939, 592-599 (1978), according to which a thromboplastin that is especially sensitive to factor VII can be prepared from the brains of dogs with congenital factor VII deficiency.

Methods have already been described for the preparation of thromboplastins of special sensitivity to factor VII. For example, the desired effect is said to be achieved in accordance with DE-AS No. 2,556,493 by extracting the tissue directly with an alkali lye. It is highly probable that the thromboplastin is damaged by this method. This is also indicated by the fact that a relatively large number of adjuvants are used in this method for the stabilization of the thromboplastin product.

Another method is given in Biochem. Soc. Trans. 8, 133, (1980), namely the adsorption of factor VII onto barium sulfate. But according to the inventor's experience the thromboplastin largely precipitates together with the barium sulfate.

The isolation of thromboplastin from the tissue of animals with congenital factor VII deficiency is out of the question for industrial application merely for reasons of cost and the scarcity of the material.

THE INVENTION

It is therefore the object of the invention to create a method of preparing thromboplastin having a sufficient and definable sensitivity to coagulation factor VII, which does not have the disadvantages of the known methods, and which makes it possible to satisfy the requirement described in the beginning.

This object is achieved in accordance with the invention by a method of making a tissue thromboplastin preparation which is sensitive to coagulation factor VII, by the preparation of acetone dry powder from mammalian tissue and extraction of the powder with salt solution, which is characterized by performing the extraction with a salt solution containing 1 to 20 mmol/l of calcium ions and a surface active substance if desired, and drying the extract if desired.

A salt solution containing 5 to 15 mmol/l of calcium ions is used preferentially for the extraction in accordance with the invention. Basically, any sufficiently water-soluble calcium salt is suitable. However, a calcium salt of a water-soluble carboxylic acid, especially formic acid or acetic acid, is preferred.

The preparation of the acetone dry powder from mammalian tissue is performed by known methods. It is described, for example, in "Human Blood Coagulation, Hemostasis and Thrombosis" (R. Biggs, Editor, Blackwell Scientific Publications, Oxford 1976, p. 663). Starting with such acetone-dried tissue preparations, it is then possible to perform the extraction of the thromboplastin in accordance with the invention. It is desirable, however, for the actual extraction of the thromboplastin to be preceded by a washing for the purpose of separating any undesirable impurities still contained in the tissue, such as hemoglobin, for example. If the washing is performed first, it is preferably done with buffer solution of a pH of about 6.5 to about 8. For example, this washing can be performed with 0.1 mol/l of sodium acetate buffer pH 7.0, and the tissue residue containing thromboplastin can be recovered by physical methods such as centrifugation. Other washing liquids, however, are also suitable. A preliminary washing of this kind does result in a certain loss of yield by the washing out of thromboplastin.

The actual extraction with a salt solution containing calcium ions can be performed with a pure calcium salt solution or with a solution of another salt to which the necessary amount of calcium ions has been added. For example, the extraction can be performed with physiological sodium chloride solution to which the stated amount of calcium ions has been added in the form of corresponding calcium salts. However, other concentrations and other salts can be used.

The addition of buffer to the extraction solution is not necessary if approximately neutral salts are used. However, if the pH of the salt solution is above or below the range of about 5.5 to 9, it is desirable to add a buffer that assures an approximately neutral pH.

Another component which may be present in the extraction solution used in accordance with the invention is a surface active agent. The surface active agent permits an increase of the yield, although it is not necessary for the achievement of factor VII sensitivity. Cationic, anionic and nonionic surface active agents are suitable. A typical example of appropriate cationic detergents is cetyl-trimethylammonium bromide, and typical examples of anionic surfactants are compounds of the gallic acid group and their salts such as cholic acid, deoxycholic acid etc. Examples of appropriate nonionic surfactants are the polyethylene oxide ethers and esters with hydrophobic alkyl, aryl and aralkyl moieties.

The amount of surface active agent appropriate in each case can be determined by simple preliminary experiment. If anionic surface active substances are involved, care must be taken that the solubility limit of the calcium salt is not exceeded. Preferably 0.01 to 0.5 weight-percent of surface active agent is added to the extraction solution, but lesser or greater amounts can also be used.

The extraction can be performed at standard or elevated temperature. At elevated temperature the yield can be increased, but the limit of about 45° C. should not be exceeded to avoid damage to the extracted thromboplastin.

Factor VII sensitivity is present if the Quick test is performed on a factor VII deficient plasma and the coagulation time is found to be substantially longer than when the same test is performed using normal plasma. The term, "factor VII deficient plasma", is to be understood to refer to a plasma which originates from persons having a congenital factor VII deficiency.

The effect achieved in accordance with the invention can be demonstrated, for example, by first washing acetone dry powder, prepared by known methods, with an acetate buffer of pH 7.0, and then with 0.85% sodium chloride solution containing 0.05% sodium deoxycholate. The thromboplastin obtained shows a high thromboplastic activity in the Quick test, for example a coagulation time of approximately 11 seconds on normal plasma. If a plasma deficient in factor VII is used instead of normal plasma, the coagulation time is found to be, for example, from 18 to 20 seconds. The thromboplastin extracted with this calcium-free extractant therefore has a low factor VII sensitivity.

However, if the acetone dry tissue is extracted with a corresponding solution containing additionally 10 mmol/l of calcium ions, the thromboplastin supernatant, after centrifugation, has a coagulation time of about 12 seconds in the Quick test with normal plasma, but with factor VII deficient plasma it has a coagulation time of 40 to 60 seconds. Therefore, in accordance with the invention a substantially higher sensitivity to a factor VII deficiency is obtained than when a known method is used involving extraction without the addition of calcium.

Characteristically, the coagulation time for normal plasma is slightly longer with thromboplastin made in accordance with the invention than it is with a preparation extracted without calcium ions. This, however, is unimportant in view of the large gain in sensitivity to factor VII. For example, if the factor sensitivity of a thromboplastin is expressed as the ratio of the coagulation time of a deficient plasma to the coagulation time of normal plasma, a thromboplastin extracted without calcium in accordance with the above example shows a ratio of approximately 1.6, but one obtained in accordance with the invention has a ratio of 4.0.

A thromboplastin with improved factor VII sensitivity can also be obtained below the specified minimum of 1 mmol/l of calcium ions, but then the sensitivity values obtained are decidedly lower, and also they are not uniform from batch to batch.

Additional subject matter of the invention is a reagent for determining the ability of the blood to coagulate, which contains thromboplastin and calcium salt, and it is characterized by the fact that it contains a tissue thromboplastin preparation made in the presence of calcium ions by the method herein described. Preferably, such a preparation will have a quite definite factor VII sensitivity. This can be accomplished by adding to the preparation another thromboplastin preparation which is insensitive to factor VII. By the appropriate selection of the amounts of factor VII sensitive and factor IV insensitive thromboplastin, any desired factor VII sensitivity can be established. This can be brought about in an especially simple manner by subjecting the residue of the extraction of the acetone dry tissue in accordance with the invention to another extraction without the addition of calcium ions. A factor VII insensitive thromboplastin fraction is thus obtained. By mixing different proportions of the two factions, it is thus possible to prepare large-scale TP batches having a definite and repeatable factor VII sensitivity. This is a considerable advance in regard to standardization and batch consistency.

A special advantage of the method of the invention lies in its simplicity and in the absence of conditions which might damage the thromboplastin.

EXAMPLES

The following examples will serve to explain the invention further.

EXAMPLE 1

(a) 10 g of acetone dry powder from rabbit brain is treated with 10 g of Supercel and incubated with 400 ml of 0.1 mol sodium acetate buffer pH 7.0, for 30 minutes at 37° C. on the water bath. Then the mixture is centrifuged for 15 minutes at 2500 g. The precipitate is suspended in 400 ml of 0.85% sodium chloride solution containing 0.05% sodium deoxycholate, and stirred on the water bath for 30 minutes at 30° C. Then it is centrifuged for 10 minutes at 2500 g. The supernatant contains factor VII insensitive thromboplastin. The precipitate is discarded.

(b) the extraction of the thromboplastin is performed under the same conditions as in Example 1a, but with the addition of 7.5 mmol/l of calcium formiate. A factor VII sensitive thromboplastin is obtained.

EXAMPLE 2

A Quick test is performed with the thromboplastin extracts prepared in accordance with Examples 1a and 1b. Since calcium is needed for the reaction, the thromoplastin extract obtained in the absence of calcium ions in Example 1 must be stocked up to 7.5 mmol/l with calcium formiate. A citrate plasma obtained from 10 healthy donors in the manner specified in DIN 58910 for the establishment of reference curves for the Quick test serves as normal plasma. The factor VII deficient plasma is a congenitally factor VII deficient plasma sold by Dade.

0.2 ml of the thromboplastin suspension preheated to 37° C. is added to each 0.1 ml specimen of plasma and the time elapsing before coagulation begins is determined using a coagulometer according to Schnittger and Gross (mfd. by Amelung of Lemgo, Federal Republic of Germany). It is found that the test thromboplastin suspension extracted in accordance with Example 1a coagulates in 10.0 seconds with normal plasma and in 16.1 seconds with factor VII deficient plasma (ratio 1.6).

The thromboplastin suspension extracted with the addition of calcium in Example 1b has a coagulation time with normal plasma of 12.3 seconds, and with factor VII deficient plasma 45 seconds (ratio 3.7).

EXAMPLE 3

Thromboplastin extracts prepared in accordance with Examples 1a and 1b, after bringing the calcium content of the calcium-free extract up to 7.5 mmol/l, are mixed in various ratios and the coagulation time is measured in accordance with Example 2 for normal plasma and factor VII deficient plasma. The results appear in Table 1. They show that, in accordance with the invention, mixtures having a specific factor VII sensitivity can be prepared.

TABLE 1

| % by volume of extract obtained w/o calcium | % by volume of extract obtained with calcium | Coagulation time with normal plasma (seconds) | Coagulation time with Factor VII deficient plasma (sec) |
| --- | --- | --- | --- |
| 100 | 0 | 10.0 | 16.1 |
| 75 | 25 | 10.5 | 17.4 |
| 50 | 50 | 11.2 | 19.5 |
| 25 | 75 | 11.1 | 23.8 |
| 12.5 | 87.5 | 11.6 | 28.8 |
| 0 | 100 | 12.3 | 45.0 |

EXAMPLE 4

For the preparation of reagent, the thromboplastin suspensions of Examples 1a and 1b are mixed in such proportions that the coagulation times for factor VII deficient plasma and normal plasma are in a ratio of 3.1. Then 2 wt.-% of glycine plus 0.01 wt.-% of merthiolate is added and the solution obtained is lyophilized.

It will be understood that the specification and examples are illustrative but not limitative of the present invention and that other embodiments within the spirit and scope of the invention will suggest themselves to those skilled in the art.

What is claimed is:

1. A method of producing a tissue thromboplastin preparation which is sensitive to coagulation factor VII comprising
extracting an acetone dry powder from mammalian tissue with an aqueous salt solution of 1 to 20 mmol/l of calcium ions.

2. The method of claim 1, wherein said salt solution contains 5 to 15 mmol/l of calcium ions.

3. The method of claim 1 wherein the calcium ions are supplied by a calcium salt of a water-soluble carboxylic acid.

4. The method of claim 3 wherein said carboxylic acid is formic or acetic acid.

5. The method of claim 1 further comprising washing the acetone dry powder with a pH 6.5 to 8 buffer solution before extracting.

6. The method of claim 1 further comprising adding a surface active agent to the extraction solution.

7. The method of claim 6 wherein 0.01 to 0.5% surface active agent is added.

8. The method of claim 1 further comprising drying the extract.

9. A reagent for the control of blood coagulating ability, comprising a factor VII sensitive tissue thromboplastin preparation obtained by extracting an acetone dry powder from mammalian tissue with an aqueous salt solution of 1 to 20 mmol/l of calcium ions.

10. The reagent of claim 9 further including a predetermined amount of factor VII insensitive thromboplastin preparation to establish a predetermined factor VII sensitivity for the reagent.

* * * * *